(12) United States Patent
Hills et al.

(10) Patent No.: US 8,486,020 B2
(45) Date of Patent: Jul. 16, 2013

(54) PRESSURE SENSOR AND METHOD OF USE

(75) Inventors: Chris Hills, Syracuse, UT (US); Mark Stringham, Salt Lake City, UT (US); Blake Allen, Murray, UT (US)

(73) Assignee: Zevex, Inc., Salt Lake City, UT (US)

( * ) Notice: Subject to any disclaimer, the term of this patent is extended or adjusted under 35 U.S.C. 154(b) by 8 days.

(21) Appl. No.: 13/206,442

(22) Filed: Aug. 9, 2011

(65) Prior Publication Data

US 2012/0203179 A1 Aug. 9, 2012

Related U.S. Application Data

(60) Provisional application No. 61/372,822, filed on Aug. 11, 2010.

(51) Int. Cl.
*A61M 5/142* (2006.01)
(52) U.S. Cl.
USPC ........................................ 604/151; 604/93.01
(58) Field of Classification Search
USPC .............................................. 604/151, 93.01
See application file for complete search history.

(56) References Cited

U.S. PATENT DOCUMENTS

| 3,209,596 A | 10/1965 | Kelly |
| 3,978,731 A | 9/1976 | Reeder et al. |
| 4,244,365 A | 1/1981 | McGill et al. |
| 4,322,978 A | 4/1982 | Fromm |
| 4,322,979 A | 4/1982 | Fromm |
| 4,373,525 A | 2/1983 | Kobayashi |
| 4,460,355 A | 7/1984 | Layman |
| 4,469,481 A | 9/1984 | Kobayashi |
| 4,554,837 A | 11/1985 | Danby et al. |
| 4,555,949 A | 12/1985 | Danby et al. |
| 4,559,034 A | 12/1985 | Kirita et al. |
| 4,612,810 A | 9/1986 | Martens |
| 4,624,413 A | 11/1986 | Corsette |
| 4,663,965 A | 5/1987 | Metcalf et al. |
| 4,762,518 A | 8/1988 | Kreinick |
| 4,784,576 A | 11/1988 | Bloom et al. |

(Continued)

FOREIGN PATENT DOCUMENTS

| EP | 0 261 860 | 3/1988 |
| EP | 0 410 187 | 1/1991 |

(Continued)

OTHER PUBLICATIONS

Honeywell Force Sensors FSS Low Profile Force Sensors FS Series (http://sensing.honeywell.com/index.php/ci_id/50137/la_id/1/document/1/re_id/0). Last visited on Nov. 21, 2012.*

(Continued)

*Primary Examiner* — Laura Bouchelle
(74) *Attorney, Agent, or Firm* — Hodgson Russ LLP

(57) ABSTRACT

A sensor and method of use provides for detection of an occlusion (or sudden pressure increase) in tubing during the administration of solutions to a patient. The occlusion sensor may be attached to an infusion pump using a biasing mechanism. The tubing may be positioned in contact with the occlusion sensor using a cassette. Detection of an occlusion in the tubing is accomplished by measuring the compression and expansion of the tubing. When the tubing becomes occluded pressure within the tube will increase, resulting in expansion of the tubing. Expansion of the tubing exerts a force on the sensor to trigger an alarm to alert medical personnel of the occluded tube.

21 Claims, 6 Drawing Sheets

U.S. PATENT DOCUMENTS

| | | | |
|---|---|---|---|
| 4,784,577 A | 11/1988 | Ritson et al. | |
| 4,863,425 A | 9/1989 | Slate et al. | |
| 4,882,575 A | 11/1989 | Kawahara | |
| 4,950,244 A | 8/1990 | Fellingham et al. | |
| 4,973,309 A | 11/1990 | Sultan | |
| 4,994,035 A | 2/1991 | Mokros | |
| 5,008,556 A | 4/1991 | Mersch | |
| 5,096,385 A | 3/1992 | Georgi et al. | |
| 5,098,380 A | 3/1992 | Aizawa et al. | |
| 5,098,384 A | 3/1992 | Abrams | |
| 5,103,211 A | 4/1992 | Daoud et al. | |
| 5,181,912 A | 1/1993 | Hammett | |
| 5,346,477 A | 9/1994 | Edwards et al. | |
| 5,438,868 A | 8/1995 | Holden et al. | |
| 5,482,446 A | 1/1996 | Williamson et al. | |
| 5,514,102 A | 5/1996 | Winterer et al. | |
| 5,531,680 A | 7/1996 | Dumas et al. | |
| D389,228 S | 1/1998 | Winterer et al. | |
| 5,704,584 A | 1/1998 | Winterer et al. | |
| 5,720,721 A | 2/1998 | Dumas et al. | |
| 5,733,061 A | 3/1998 | Child | |
| 5,741,216 A | 4/1998 | Hemmingsen et al. | |
| 5,746,756 A | 5/1998 | Bromfield et al. | |
| 5,789,675 A | 8/1998 | Blaine et al. | |
| 5,808,203 A * | 9/1998 | Nolan et al. | 73/700 |
| 5,810,323 A | 9/1998 | Winterer et al. | |
| 5,844,587 A | 12/1998 | Ando et al. | |
| 5,860,938 A | 1/1999 | Lafontaine et al. | |
| 5,964,377 A | 10/1999 | Demarest et al. | |
| 5,983,725 A | 11/1999 | Fischer et al. | |
| 5,984,149 A | 11/1999 | Thanisch et al. | |
| 6,012,342 A | 1/2000 | Blight et al. | |
| 6,023,970 A | 2/2000 | Blaine | |
| 6,116,472 A | 9/2000 | Wanbaugh et al. | |
| 6,142,979 A | 11/2000 | McNally et al. | |
| 6,192,752 B1 | 2/2001 | Blaine | |
| 6,328,720 B1 | 12/2001 | McNally et al. | |
| D455,489 S | 4/2002 | Beck et al. | |
| 6,463,813 B1 | 10/2002 | Gysling | |
| 6,506,035 B1 | 1/2003 | Beck | |
| 6,523,414 B1 | 2/2003 | Malmstrom et al. | |
| 6,531,708 B1 | 3/2003 | Malmstrom et al. | |
| 6,543,885 B2 | 4/2003 | Bahl et al. | |
| 6,595,950 B1 | 7/2003 | Miles et al. | |
| 6,623,447 B2 | 9/2003 | Miles et al. | |
| 6,636,010 B1 | 10/2003 | Malmstrom et al. | |
| 6,659,976 B2 | 12/2003 | Beck et al. | |
| 6,685,670 B2 | 2/2004 | Miles et al. | |
| 6,749,591 B1 | 6/2004 | McNally et al. | |
| 6,750,468 B2 | 6/2004 | Malmstrom et al. | |
| D501,924 S | 2/2005 | Cise et al. | |
| 6,852,094 B2 | 2/2005 | Beck et al. | |
| D503,799 S | 4/2005 | Beck | |
| D503,978 S | 4/2005 | Beck | |
| D504,506 S | 4/2005 | Beck et al. | |
| D505,199 S | 5/2005 | Beck et al. | |
| 6,902,541 B2 | 6/2005 | McNally et al. | |
| 6,907,788 B2 | 6/2005 | Malmstrom et al. | |
| D507,647 S | 7/2005 | Beck et al. | |
| 6,923,785 B2 | 8/2005 | Miles et al. | |
| 6,979,311 B2 | 12/2005 | Miles et al. | |
| D523,553 S | 6/2006 | Beck et al. | |
| 7,070,575 B2 | 7/2006 | Beck et al. | |
| 7,121,143 B2 | 10/2006 | Malmstrom et al. | |
| 7,150,727 B2 | 12/2006 | Cise et al. | |
| D536,783 S | 2/2007 | Cise et al. | |
| 7,367,963 B2 | 5/2008 | Cise et al. | |
| 7,419,478 B1 * | 9/2008 | Reilly et al. | 604/241 |
| 2002/0169424 A1 | 11/2002 | Miles et al. | |
| 2004/0220542 A1 | 11/2004 | Cise | |
| 2005/0004540 A1 | 1/2005 | McNally | |
| 2005/0119625 A1 | 6/2005 | Miles et al. | |
| 2006/0058740 A1 | 3/2006 | Cise | |
| 2007/0118078 A1 | 5/2007 | McNally | |
| 2007/0151346 A1 | 7/2007 | Malmstrom et al. | |
| 2008/0098798 A1 | 5/2008 | Riley | |
| 2008/0103445 A1 | 5/2008 | Blaine et al. | |
| 2008/0119782 A1 | 5/2008 | Steinman | |
| 2008/0134750 A1 | 6/2008 | Riley | |
| 2008/0208117 A1 | 8/2008 | Steinman | |
| 2009/0049919 A1 | 2/2009 | Hills | |
| 2009/0149801 A1 | 6/2009 | Crandall | |
| 2009/0254034 A1 | 10/2009 | Beck | |
| 2011/0130741 A1 * | 6/2011 | Miles et al. | 604/500 |

FOREIGN PATENT DOCUMENTS

| | | | |
|---|---|---|---|
| JP | S56-31758 | | 3/1981 |
| JP | S58-163860 | | 10/1983 |
| JP | H02-01805 | | 8/1990 |
| JP | 3-205060 A | | 9/1991 |
| JP | 03205060 A | * | 9/1991 |
| WO | WO 96/08666 | | 3/1996 |
| WO | WO 98/04301 | | 2/1998 |

OTHER PUBLICATIONS

WIPO, International Searching Authority ISA/KR, International Search Report issued Mar. 9, 2012 in International Application No. PCT/US2011/047298.

The International Bureau of WIPO, International Application No. PCT/US2011/047298, Internatioanl Preliminary Report on Patentability Feb. 12, 2013.

* cited by examiner

PRESSURE SENSOR AND METHOD OF USE

RELATED APPLICATIONS

The present application claims the benefit of U.S. Provisional Application Ser. No. 61/372,822, filed Aug. 11, 2010, which is herein incorporated by reference in its entirety.

BACKGROUND OF THE INVENTION

1. The Field of the Invention

The present invention relates to an apparatus and method for detecting occlusions and other pressure changes during administration of solutions to a patient. More particularly, the present invention relates to a force sensor for an infusion set which detects occlusions in a tube during administration of a solution to a patient.

2. State of the Art

Treating a patient often requires administering to the patient certain fluids, medication or other nutrients in solution form. The physical condition of a patient may require enteral feeding of a nutrient solution into a patient's stomach or bowel. Likewise, a patient may require parenteral or intravenous infusion of medication, hydration and/or nutrients. Furthermore, there are times when a pressurized solution is provided to a patient to clean out diseased tissue or a wound.

In enteral feeding, it is important to provide the solution within a desired pressure range to ensure the solution, which can be somewhat viscous, is delivered, but at a pressure which is not uncomfortable to the patient or which could damage tissue surrounding the outlet of the feeding set. While controlling pressure is a concern, medical personnel must also be concerned about possible occlusion of the feeding set which prevents delivery of the feeding solution. This can be caused by a blockage within the feeding tube by, for example, materials in the feeding solution, or externally by the feeding set being crimped or otherwise obstructed by the patient or some other cause.

Likewise in parenteral feeding, it is important to deliver the solution to the patient as the patient may require the medication, fluids or nutrition in the infused solution in order to survive. As with enteral feeding, the infusion of solutions parenterally should be done at a pressure low enough to avoid damage to the veins while at sufficient pressure to assure delivery of the solution. Likewise, it is also important to ensure that flow of the solution has not been occluded.

Other situations which require delivery of solutions have similar concerns. For example, irrigation of wounds to remove bacteria and foreign material is an essential of wound management. Conventional methods of irrigating a wound include gravity flow and bulb syringe procedures. However, considerable practice variation exists in the details of technique. An important factor in wound irrigation is volume; increased volume improves wound cleansing to a point, but the optimal volume is unknown. Additionally, high-pressure flow has been shown to remove more bacteria and debris and to lower the rate of wound infection compared with low-pressure irrigation, but high-pressure flow may lead to increased wound trauma which, in turn, increases the time for a wound to heal. Similarly, antiseptic additives can kill bacteria in the wound, but host-tissue toxicities may limit their use.

According to principles of the present invention, to overcome the inherent variability of conventional wound irrigating procedures, solutions can be administered to the patient using an infusion pump. Administering solutions to patients using an infusion pump is well known in the medical arts. Infusion pumps are often used to deliver fluids, medications or nutrients from a reservoir to the patient via tubing. The use of an infusion pump allows for the continuous or periodic delivery of these solutions to the patient without the need of constant supervision by medical personnel. Moreover, infusion sets that utilize a pump, or some other apparatus to apply a positive force to the solution in the tubing to facilitate flow, can more precisely control the rate and timing of delivery. With controlled infusion using an infusion pump, the solution can be delivered at a precise rate that will keep the solution's concentration within the therapeutic margin and out of any potentially cytotoxic range.

While the use of an infusion pump to deliver medications and other solutions has the advantages described above, there is a risk that flow of a solution through the tubing may become impeded, resulting in the patient not receiving needed fluids and medications. For example, a patient may unintentionally roll onto the tubing thereby compressing the tubing and stopping or reducing the flow, or, a blood clot or other debris may block the flow of solution through the tubing. To overcome these types of problems standard safety features on modern infusion pumps include a downstream sensor to detect changes in flow of a solution through the tubing and to warn medical personnel when the tubing is impeded.

Furthermore, it has been found that irrigating wounds at pressures below 4 pounds per square inch (psi) may not adequately cleanse the wound. Thus, for example, more optimum irrigation pressures may be between 6-14 psi and may preferably be about 8-12 psi to be more effective at cleansing the wound and reducing wound trauma and wound infection. Therefore, it is desirable to have a sensor that is capable of detecting a change in pressure within the tubing in these ranges when using an infusion pump to deliver solutions to a patient's wound.

Thus, there is a need for a sensor that produces a signal that is easily discernable between atmospheric pressure and a desired in-line tubing pressure (e.g. 4 psi, 8 psi, 10 psi, etc.) to allow for the continuous and precise delivery of solutions during enteral feeding, parenteral solution infusion, wound irrigation, or the like to improve delivery. It is also desirable to provide such a device which is relatively inexpensive and easy to use.

SUMMARY OF THE INVENTION

It is an object of the present invention to provide an apparatus and method for detecting occlusions or pressure changes during administration of solutions to a patient.

According to one aspect of the present invention, an occlusion sensor may be disposed along the infusion set. The occlusion sensor may be configured to detect a change in pressure within the tubing of the infusion set by measuring changes in the force exerted by the tubing wall on the occlusion sensor.

According to another aspect of the present invention, an occlusion sensor system may include a plunger with a first end which protrudes through a collar to selectively engage the tubing of an infusion set. The plunger may also include a second end which engages a sensor. A change in pressure within the tubing of the infusion set may results in a change in force exerted by the tubing wall against the first end of the plunger which may be communicated to the sensor via the second end of the plunger. The force exerted on the sensor may produce a voltage output relative to the force induced by the tubing.

In accordance with another aspect of the present invention, an occlusion sensor may be located on a printed circuit board, and the printed circuit board may be attached to the pump of an infusion set.

In accordance with still another aspect of the present invention, an occlusion sensor may be located on a printed circuit board, and the printed circuit board may be attached to the pump of an infusion set using a biasing mechanism.

According to another aspect of the present invention, a cassette may be provided that may be removably attached to the pump of the infusion set. The cassette may be configured to hold the tubing of the infusion set and position the tubing in communication with an occlusion sensor.

According to still another aspect of the present invention, the cassette may include retaining members or projections which engage the collar of the occlusion sensor.

According to yet another aspect of the present invention, the cassette may be disposable.

In accordance with a further aspect of the present invention, an occlusion sensor system may include a collar, a plunger, and a sensor mounted on a pump. A cassette having retaining members and configured for receiving an infusion set may be removably attached to the pump opposite the sensor, with the retaining members of the cassette contacting the collar of the occlusion sensor. A first end of the plunger may protrude through the collar of the occlusion sensor to engage the tubing of the infusion set. A change in pressure inside the tubing may exert a force on the first end of the plunger; the force may then be transferred through the plunger to a second end of the plunger. The second end of the plunger may be adjacent the sensor so that the force may be applied to the sensor and a voltage output produced relative to the magnitude of the force.

In accordance with yet another aspect of the present invention, an occlusion sensor system may include a sensor located on or adjacent to a printed circuit board attached to a pump using a biasing mechanism. A cassette having retaining members may be removably attached to the pump opposite the sensor, with the retaining members of the cassette contacting a collar of the occlusion sensor system. The occlusion sensor system may also include a plunger, wherein the first end of the plunger may protrude through the collar of the occlusion sensor to engage tubing of an infusion which may be held by the cassette. The second end of the plunger may exert a force on the sensor which produces a voltage output relative to a force induced by the tubing.

In accordance with still another aspect of the present invention, an occlusion sensor system may include a sensor located on a printed circuit board which may be attached to a pump using a biasing mechanism. A cassette, without retaining members, may be removably attached to the pump opposite the sensor. The first end of a plunger associated with the sensor may protrude through a collar of the occlusion sensor system to engage the tubing of an infusion set, which may be held by the cassette. The second end of the plunger may exert a force on the sensor which produces a voltage output relative to a force induces by the tubing. By eliminating the retaining members on the cassette channel, the force induced by the biasing mechanism, such as springs, may be exerted directly on the tubing. The advantages of this aspect of the present invention may include application of a consistent force between the collar and tubing. This force, along with a fixed protrusion distance of the plunger, may normalize the initial cassette loaded force and minimize the effects of differences in tubing properties. An additional advantage may be that the force induced by the biasing mechanism may press the tubing into an oval shape. The oval shape of the tubing may reduce the force effects of the side walls of the tubing, thus making the overall tubing more compliant in the area of measurement. This increased flexibility in the tubing may reduce the effects of differences in tubing properties and aid in making a more direct measurement of the force induced by an occlusion.

These and other aspects of the present invention are realized in occlusion sensors and methods of use as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The various elements of the invention accomplish various aspects and objects of the invention. It is appreciated that not every element of the invention can be clearly displayed in a single drawing, and as such not every drawing shows each element of the invention.

DETAILED DESCRIPTION

The drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
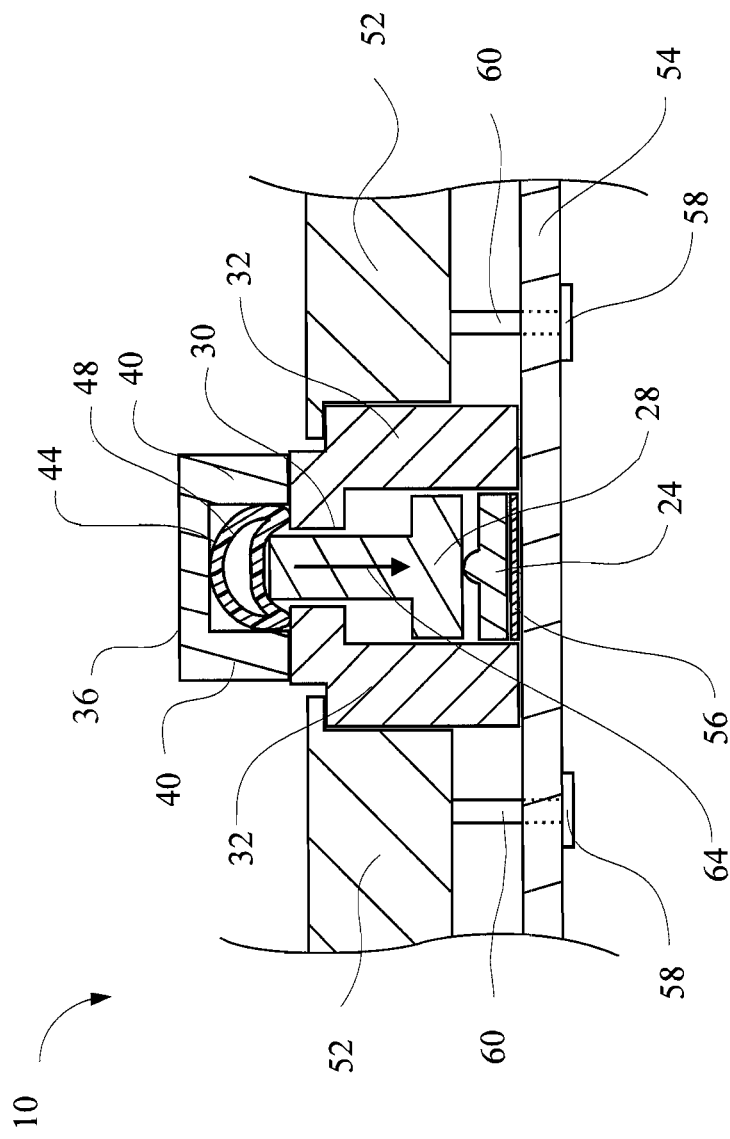
FIG. 1 shows a cross-sectional view of one application of an occlusion sensor made in accordance with the principles of the present invention, disposed on a pump body for an infusion set.

Turning to FIG. 1, there is shown a cross-sectional view of one application of an occlusion sensor system, generally indicated at 10, in accordance with principles of the present invention. The occlusion sensor system 10 may be disposed on a pump body 52 (a fragmented view of which is shown). The pump is configured to pump fluid through a structure, such as tubing 44 of an infusion set. The pump may be, for example, a peristaltic pump, or other type of pump used to deliver solutions to a patient. As shown below, the occlusion sensor system 10 extends through the pump body 52 and would typically, but not necessarily, be positioned adjacent to the pumping mechanism, such as a peristaltic pump roller.

The occlusion sensor system 10 may include a sensor 24 located on or adjacent to a printed circuit board 56, such as a piezoresistive sensor. The printed circuit board 56 may be disposed on a mounting plate 54 which may be attached to the pump body 52 using, for example, screws 60, although it will be appreciated that the mounting plate 54 could also be attached to the pump body 52 using a variety of other methods. Additionally, it will be appreciated that printed circuit board 56 may be mounted directly to the pump body 52 (See FIG. 2), thus obviating the need for a mounting plate 54.

The occlusion sensor system 10 may also include a collar 32, and a plunger 28. Plunger 28 may extend through an opening 30 in the collar 32 to contact the tubing 44 of an infusion set when the tubing 44 is held adjacent to the pump body 52. According to one aspect of the invention, the tubing 44 may be held adjacent the pump body 52 using a cassette 36 and the plunger may protrude a distance into the tubing 44.

Cassette 36 may also position the tubing 44 adjacent to plunger 28 to facilitate engagement of the plunger 28 with tubing 44. Projections or retaining members 40 on the cassette 36 may help to prevent or minimize lateral spreading of the tubing 44 depending on the distance the retaining members 40 are spaced apart and the diameter of the tubing 44. As shown in FIG. 1, the sensor 24 may remain in a substantially fixed position relative to the tubing 44 when the occlusion sensor system 10 is in use.

When in contact with plunger 28, tubing 44 may exert a force on the plunger 28, represented by arrow 64. For example, under one set of conditions during use of the occlusion sensor system 10, an occlusion of the tubing 44 may occur downstream from the occlusion sensor system 10, which may cause the pressure in the tubing 44 to increase and lead to an expansion of the tubing 44. Expansion of the tubing 44 may exert a force 64 on the plunger which differs in magnitude as compared to the force 64 which is exerted on the tubing 44 when tubing 44 is not occluded. The force 64 may be communicated to the sensor 24 via the plunger 28. The sensor 24 located on the printed circuit board 56 may produce a voltage output relative to the increase in force 64 induced by the tubing 44. If the magnitude of the force 64 differs sufficiently during use of the occlusion sensor system 10, e.g. when tubing 44 is becomes occluded (or otherwise has a pressure which is above or below desired operational parameters) then a warning signal may be sent to alert medical personal of the improper functioning of the infusion set. The mechanism for sending the alarm may be disposed on the circuit board or may be an independent structure in communication with occlusion sensor. The warning signal may include a visual alarm, audible alarm, physical alarm, etc. Additionally, if an occlusion causes the magnitude of the force 64 applied to sensor 24 to change significantly, pump 52 may be turned off until the infusion set has been checked of fixed. According to principles of the present invention the sensor 24 may be a piezoresistive sensor, such as the Honeywell P/N FSS 1550, however, other sensors may also be used.

It has been found that the baseline voltage measurement produced by the occlusion sensor system 10 of FIG. 1 may be sensitive to dimensional tolerances of the overall assembly as well as differences associated with variance in tubing properties. In the event of an occlusion of the tubing 44 downstream from the occlusion sensor system 10, the pressure in the tubing 44 may increase, causing the tubing 44 to expand and exert a force on the plunger 28, which ultimately may lead to the detection of the occlusion by the occlusion sensor system 10.

The occlusion sensor system 10 may also be able to detect an occlusion in the tubing 44 upstream of the sensor system 10. An upstream occlusion in tubing 44 may cause the pressure inside tubing 44 to decrease which may lead to further contraction of the tubing side walls 48. As the tubing side walls 48 contract the force exerted on the sensor 24 via the plunger 28 may decrease resulting in a detectable change in the voltage output by sensor 24. Thus, an upstream occlusion may be detected in tubing 44 by sensing a drop in pressure inside tubing 44 relative to the pressure inside tubing 44 under normal operating conditions.

Figure 2:
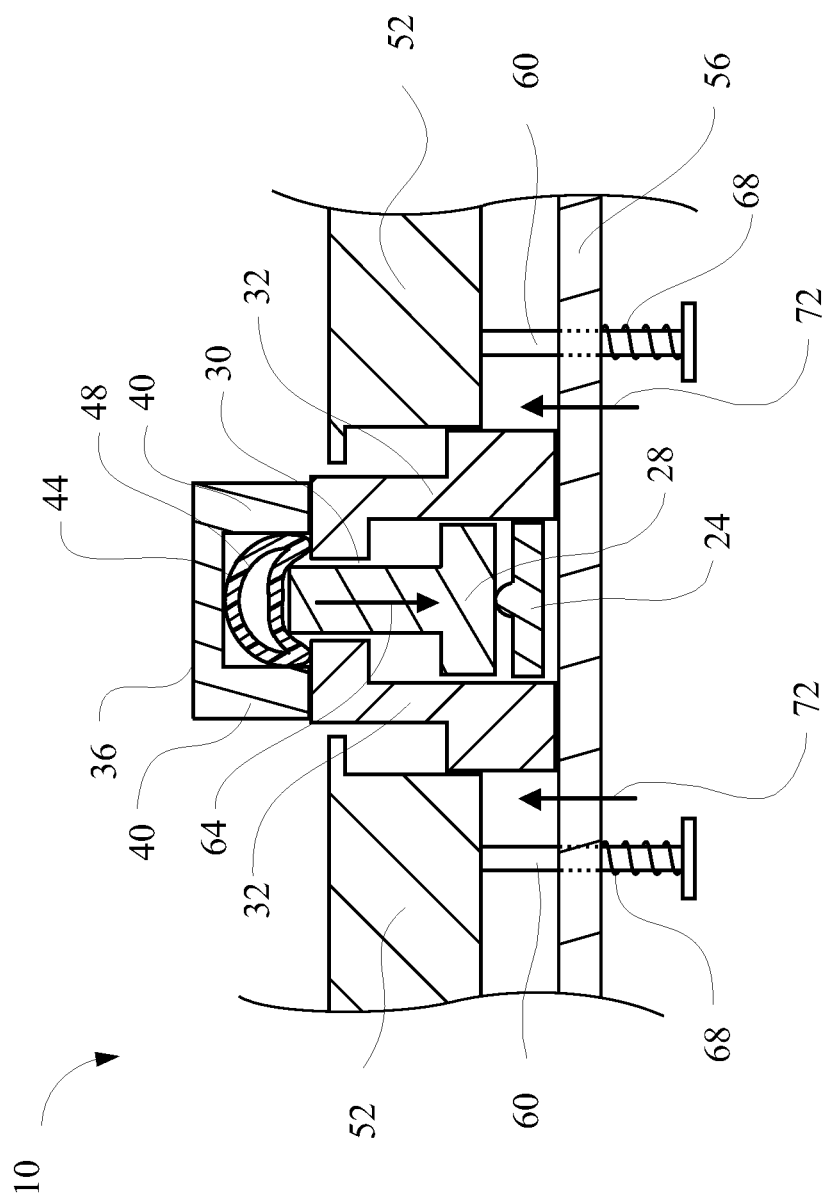
FIG. 2 shows a cross-sectional view of another application of an occlusion sensor made in accordance with the principles of the present invention, disposed on a pump body for an infusion set.

Turning now to FIG. 2, there is shown a cross-sectional view of an alternate application of the occlusion sensor of the present invention, generally indicated at 10. As with the application discussed above, the occlusion sensor system 10 is disposed on or attached to a pump or pump body 52 which may be used with an infusion set. A printed circuit board 56 may be attached to the pump body 52 directly using a biasing mechanism 68, such as springs, compressible washers, elastics and the like. This may allow the printed circuit board 56 to move relative to the pump body 52 and bias the sensor toward the plunger 28 and the plunger against the tubing 44. It has been found that more accurate results may be achieved by providing a small amount of pressure against the tubing with the plunger 28.

The collar 32 may contact retaining members 40 of the cassette. The collar 32 can act as a repeatable spacer, effectively isolating the sensor element 24, so that the sensor 24 is substantially acted upon only by the force transmitted from the expansion of the tubing 44 through movement of the plunger 28. Furthermore, because the retaining members may direct movement of the tubing 44 downward (i.e. toward the plunger 28) by limiting lateral expansion, higher signal sensitivity may be achieved.

When the cassette 36 is attached to the pump 52, the plunger 28 of the occlusion sensor system 10 engages the tubing 44. The biasing mechanism 68, together with the collar 32 and the retaining members 40, limit the distance that plunger 28 is able to protrude through the opening 30 and into the tubing 44. It has been found that the occlusion sensor system 10 of FIG. 2 may produce more accurate and consistent detection of pressure variation within the tubing 44 as compared with the occlusion sensor system of FIG. 1.

Figure 3:
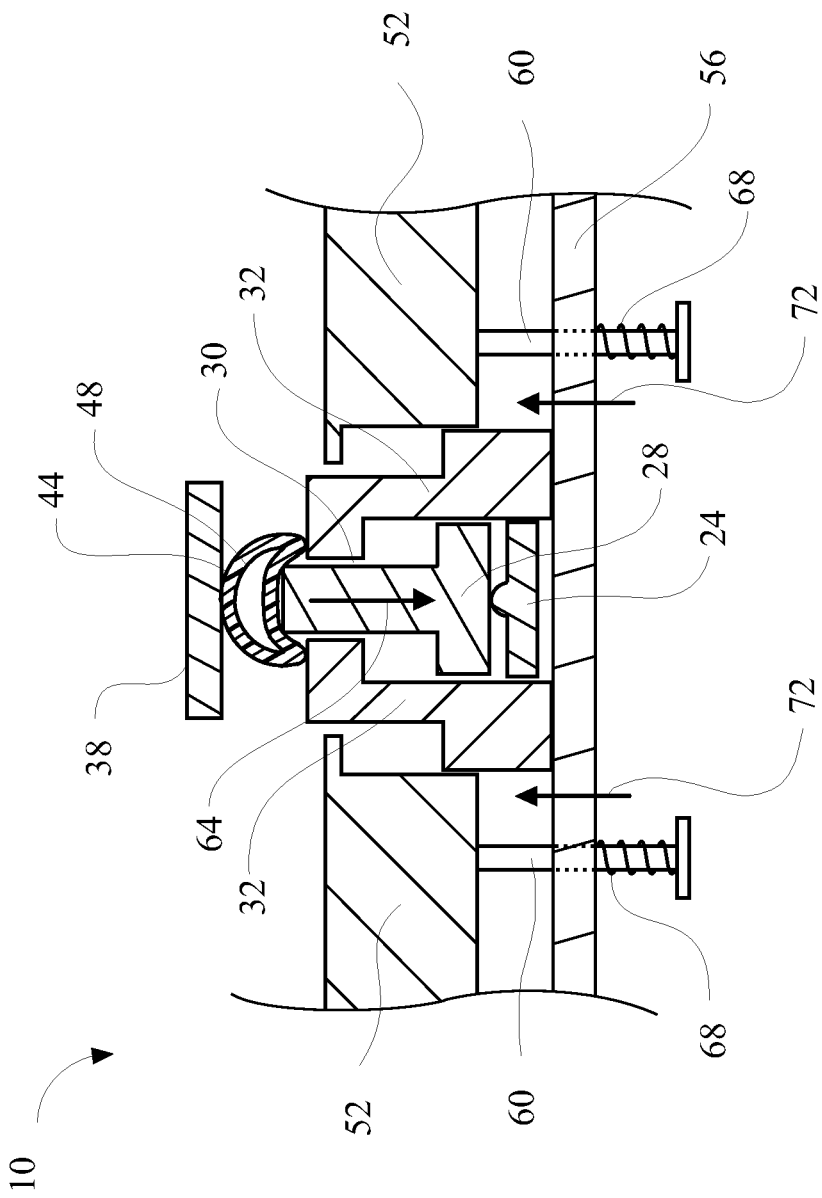
FIG. 3 shows a cross-sectional view of another application of an occlusion sensor made in accordance with the principles of the present invention, disposed on a pump body for an infusion set.

Referring now to FIG. 3, there is show a cross-sectional view of still another application of the occlusion sensor system of the present invention, generally indicated at 10, disposed on a pump 52 for an infusion set. The cassette 38 may be removably attached to the pump 52. The cassette 38 does not include retaining members or projections adjacent where the tubing 44 engages the plunger 28, in contrast to cassettes 36 shown in FIG. 1 and FIG. 2. By eliminating the retaining members on the cassette 38, the force, represented by arrows 72, induced by the biasing mechanism 68 may be exerted on tubing 44. The biasing mechanism 68 may apply a consistent force 72 to the collar 32 via the printed circuit board 56 which, in turn, may bias the collar against tubing 44 to allow force 72 to be exerted on tubing 44. Additionally, the collar 32 may have at least one shoulder 32a for engaging tubing 44 when collar 32 is biased against tubing 44. Engagement of the collar 32 with tubing 44 may limit the distance that plunger 28 protrudes through the opening 30 and into the tubing 44. It has been found that regulating the protrusion distance while applying force 72 to the tubing 44 may help normalize the force 64 induced by tubing 44 when the cassette 38 is initially removably attached to the pump 52. When the initial force 64 is normalized, the occlusion sensor system 10 shown in FIG. 3 may be less affected by variances within tubing properties.

Furthermore, the section of tubing 44 where force 72 is applied to the tubing 44 the section of the tubing 44 may partially collapse or press into an oval shape, which can be seen in the cross-sectional view depicted in FIG. 3, under ambient or normal operating conditions. The oval-shaped section of tubing 44 may reduce the force effects of the side wall 48 of the tubing 44, thus making the tubing 44 more compliant in the area of measurement, namely, where the plunger 28 contacts the side wall 48. The increase in compliance of the tubing 44 may increase the occlusion sensor system's 10 accuracy and sensitivity when measuring an increase in pressure within the tubing 44 due to a downstream occlusion. The increased compliance of the tubing 44 may also reduce the effects of tubing properties on pressure measurement taken by occlusion sensor system 10.

It has been found that the occlusion sensor system 10 and the cassette 38 according to FIG. 3, may produce voltage data that is more precise when tested with tubing having different properties as compared to the occlusion sensor system 10 and the cassette 36 of FIG. 2. Furthermore, the occlusion sensor system 10 of FIG. 3 may produce a significant increase in the voltage difference between atmospheric pressure and 10 psi without increasing the variability of voltage signals produced.

An important factor for accurately determining a pressure difference in tubing of an infusion set according to principles of the present invention may be application of the appropriate amount of force 72 induced by the biasing mechanism 68. To determine the ideal force 72 to be applied to tubing 44, data was collected using both the cassette 38 (no retaining members) and the cassette 36 (FIG. 2 with retaining members 40) on tubing with differing properties. The expected results when using cassette 36, even when tubing with different properties was used, was that varying the force 72 exerted by biasing mechanism 68 would have minimal effect on voltage output because force 72 was being exerted on the retaining members 40 as opposed to the tubing itself. Surprisingly, it was found that the voltage measurement of occlusion sensor system 10, when tested with the cassette 36, was sensitive to tubing properties. More specifically, voltage measurements on less compliant tubing, as would be expected with new tubing, when using the cassette 36 were higher than voltage measurements on tubing that had been repeatedly pressurized. This result was observed even when force 72 exerted by the biasing mechanism 68 was varied. Thus, the occlusion sensor system 10, when used in connection with the cassette 36, is sensitive to changes in tubing properties over the life of the tubing.

In contrast, when the occlusion sensor system 10 is used in connection with the cassette 38 (no retaining members) voltage measurement were less affected by a change in tubing properties. Voltage measurement using occlusion sensor system 10 in connection with the cassette 38 were taken at both atmospheric pressure and 10 psi with a force 72, ranging from 1.0 pounds to 3.0 pounds, applied to the tubing 44. The same measurements were taken using new tubing and tubing that had been repeatedly pressurized to simulate tubing that has aged. It was found that a desirable amount of force 72 to be applied to tubing 44 was in the range of about 1.2 pounds to 1.8 pounds. Although tubing properties did have a small effect on voltage measurements when the cassette 38 was used in connection with occlusion sensor system 10, this effect was minimal when compared to voltage measurements obtained when occlusion sensor system 10 was used with the cassette 36 removably attached to the pump 52.

According to one aspect of the present invention, three springs may be used as the biasing mechanism 68. Thus, to exert a force in the range of 1.2 pounds to 1.8 pounds on the tubing 44, as described above, each spring should apply approximately 0.4 to 0.6 pounds. It will be appreciated that it is not essential to the present invention that three springs be used as the biasing mechanism 68.

Figure 4:
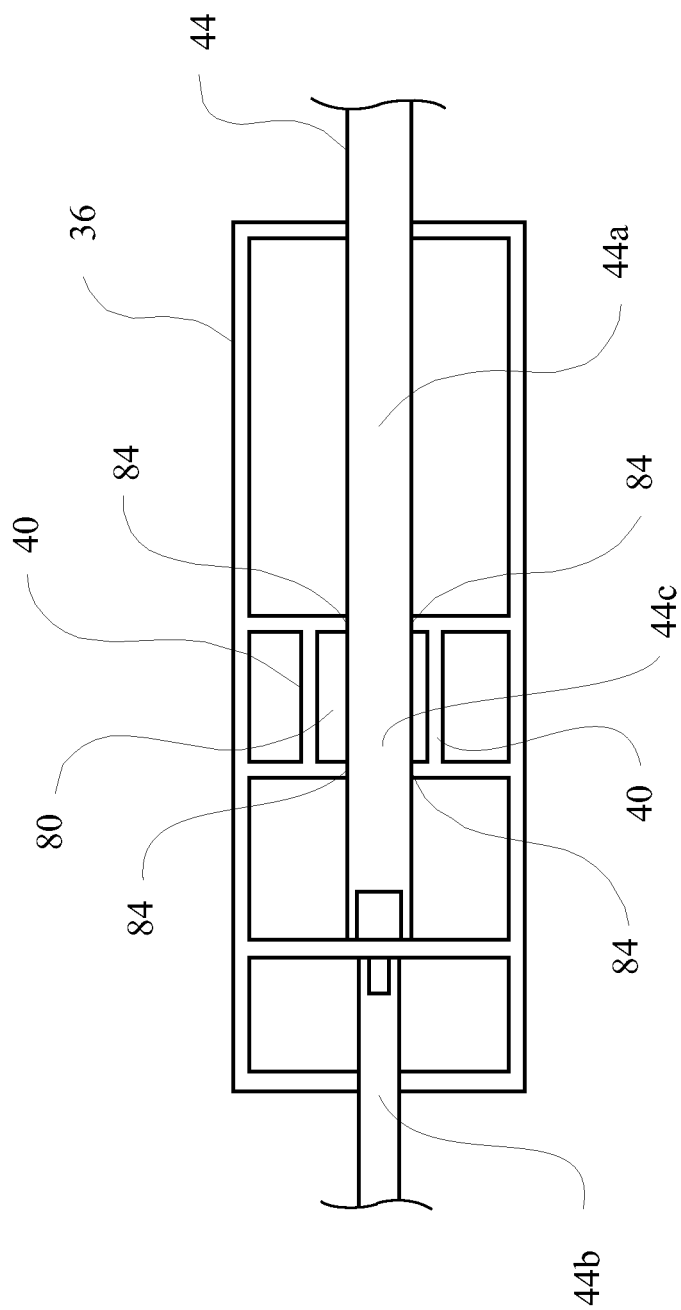
FIG. 4 shows a bottom view of the cassette of FIG. 1 and FIG. 2.

Now turning to FIG. 4, there is shown a bottom view of the cassette 36 discussed regarding FIGS. 1 and 2. The cassette 36 may include formations 84 configured to hold a segment of the tubing 44c along a channel 80 for positioning the tubing segment 44c to contact the plunger 28 of the occlusion sensor system 10 when the cassette 36 is attached to a pump. When used with a roller driven peristaltic pump, for example, the pump roller may typically engage the tubing along segment 44a, adjacent to the tubing segment 44c disposed between the retaining members 40.

Also shown are the retaining members 40 which, when cassette 36 is removably attached to the pump, may contact and engage the collar 32 to help regulate the distance that the plunger 28 is able to protrude through the opening 30, as can more clearly be seen in FIG. 2.

Figure 5:
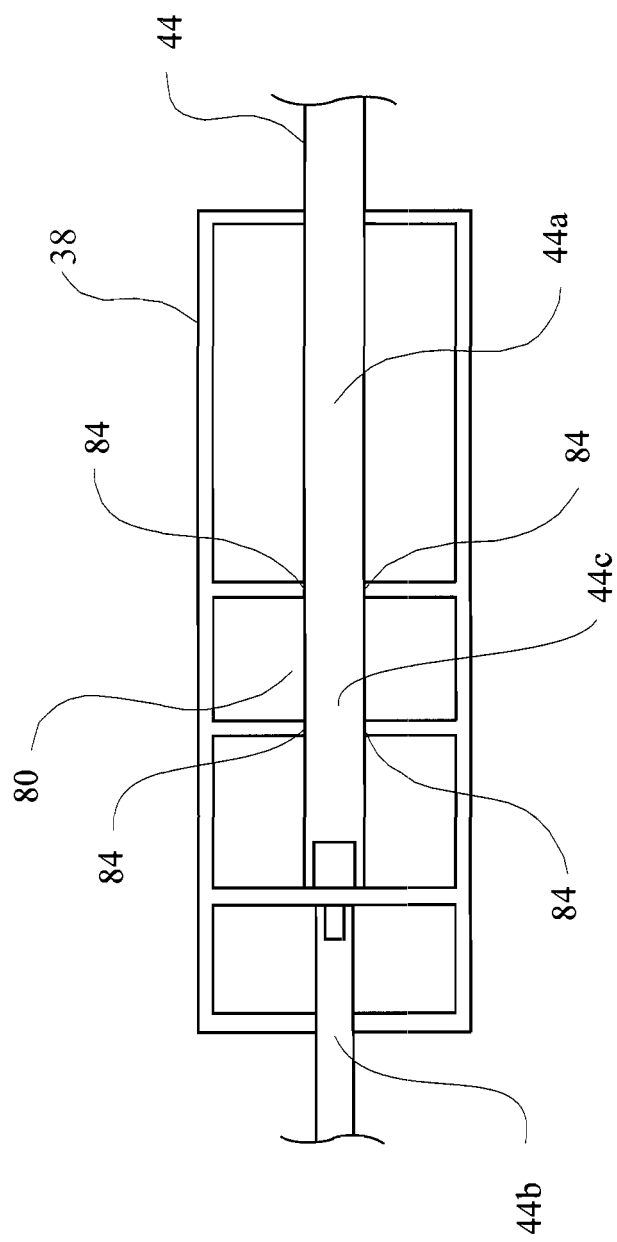
FIG. 5 shows a bottom view of the cassette of FIG. 3, without retaining members.

Referring now to FIG. 5, there is shown a bottom view of the cassette 38 of FIG. 3. In contrast to cassette 36, cassette 38 may be formed without retaining members to contact the collar 32. By eliminating the retaining members on cassette 38, the force induced by the biasing mechanism 68 (FIG. 3) may be exerted on the tubing 44. Some advantages of exerting the force induced by the biasing mechanism 68 on the tubing 44 are explained above, and may include an increase normalization of the force induced by the tubing 44 on the plunger 28, and also increasing the compliance of the tubing 44 at the position the plunger 28 contacts the tubing 44, thereby increasing the accuracy and sensitivity of pressure measurements.

Figure 6:
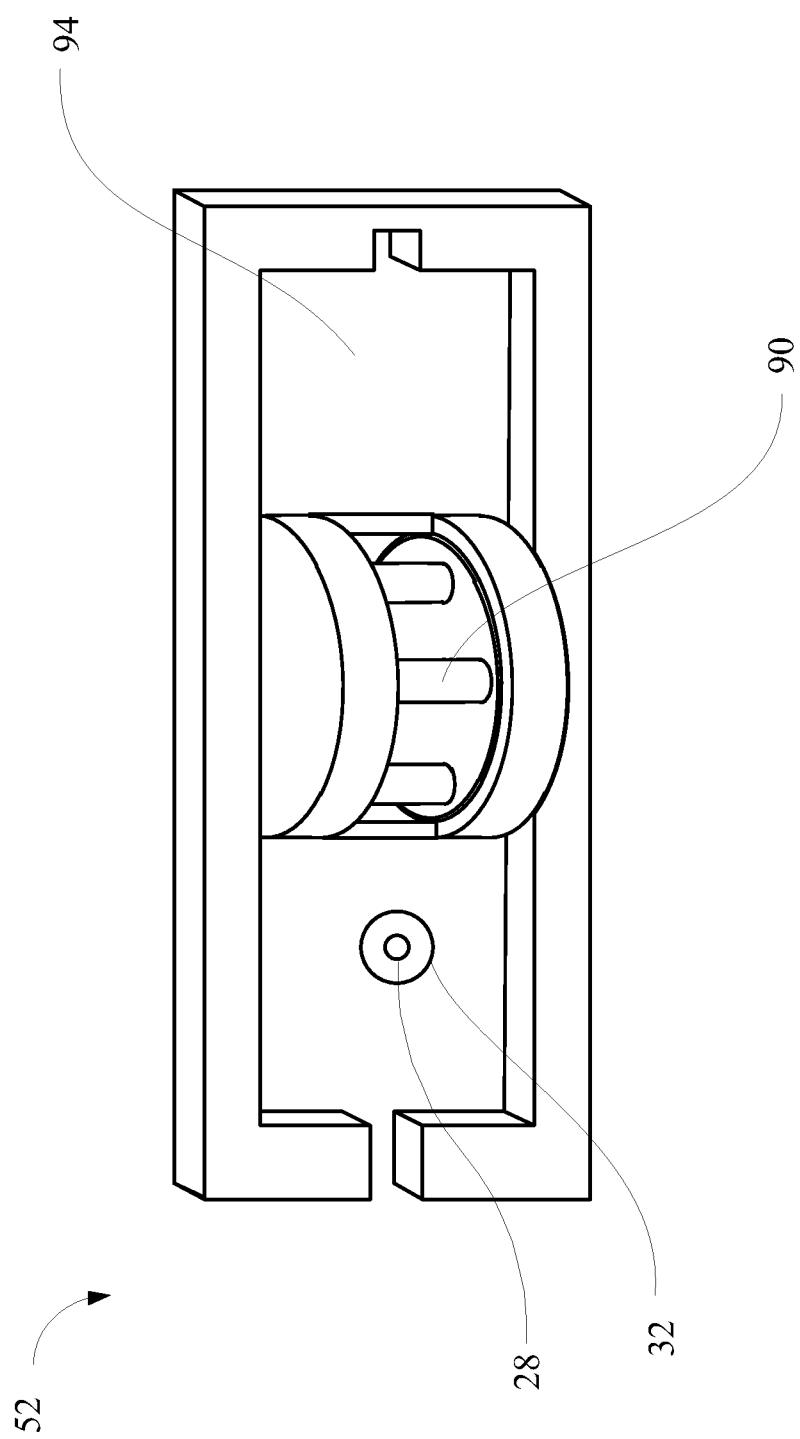
FIG. 6 shows a top view of a pump for an infusion set which can be used in accordance with the principles of the present invention.

Now turning to FIG. 6, a top, fragmented view of a pump for an infusion set, generally indicated at 52, is shown. According to one aspect of the present invention, a rotary peristaltic pump mechanism 90 may be used to facilitate the flow of solutions through the tubing 44 (FIGS. 1-5) of the infusion set. It should be appreciated that pumps, other than rotary peristaltic pumps, may be used according to principles of the present invention.

The cassette 36 or the cassette 38 may be removably attached in the recessed formation 94 in the body of the pump 52 so that the cassette holds the tubing 44 (FIGS. 1-4) in engagement with the pump mechanism 90. The cassette 36 or 38 also holds the tubing of the infusion set in communication with the plunger 28 and potentially the collar 32 of the occlusion sensor system 10. Thus, it will be appreciated that the occlusion sensor system 10 may extend completely through the pump body 52. In the alternative, the occlusion sensor system 10 could simply be recessed into a pump body having a greater depth.

It will be understood that the cassette 36 (FIG. 4) or the cassette 38 (FIG. 5) could be attached using a variety of methods and to a variety of pumps. Clips, tabs, flanges, pressure fits or a variety of other mechanisms can be used to ensure that the cassette 36 or 38 stays in the recess 94. In the alternative, the pump 52 may lack a recess and the cassette 36 or 38 may be held to an outer wall of the pump 52.

When the cassette 36 or the cassette 38 is attached to the pump 52, the tubing 44 may be positioned over the plunger 28 thereby facilitating contact between the plunger 28 and the tubing 44. Furthermore, when the cassette 36 is attached to the pump 52, the retaining members 40 may be in contact with the collar 32 to resist movement of the collar 32 into forceful contact with the tubing 44. Thus, when the occlusion sensor of the present invention is used in conjunction with a pump, an infusion system is provided which can be used with a cassette bearing tubing of an infusion set to detect occlusions and ensure that proper solution volume and/or pressure is achieved.

While the discussion above has been principally in the context of an occlusion sensor which could be used in the administration of fluids to a patient, it will be understood that the occlusion sensor could be used in a variety of non-medical applications. Either way, the occlusion sensor system 10 detects pressure change along the tubing 44 of an infusion set and can thereby create a warning that a predetermined pressure within the tubing has been exceeded. This could then be used to generate a warning signal, such as a light or audible alarm, and/or could be used to turn off the pump until the infusion set has been checked. Thus, proper pressures can be maintained by medical personnel with the occlusion sensing system 10 indicating a range outside of predetermined parameters.

It will be appreciated that various aspects of the invention discussed above can be used all together, individually or in various combinations. Thus, an occlusion sensor system may comprise a sensor for measuring the pressure inside a structure and a movable plunger disposed in communication with the structure and the sensor, wherein the movable plunger applies a force against the sensor and is oriented so that, the magnitude of the force applied to the sensor by the movable plunger changes relative to a change in pressure inside the structure. The occlusion sensor system may also have; a) the structure disposed adjacent the plunger and the structure comprising tubing of an infusion set; b) the sensor may be disposed on a pump having a pump mechanism with the tubing positioned adjacent the sensor and the pump such that the tubing is in communication with the movable plunger and the pump mechanism; c) a biasing mechanism which biases the occlusion sensor toward the plunger; d) a collar, wherein the movable plunger extends through an opening in the collar to contact the structure whose pressure is being measured; e) structure as tubing of an infusion set and wherein the occlusion sensor further comprises a collar disposed about the plunger and a biasing mechanism which biases the occlusion sensor toward the plunger and biases the collar into engagement with tubing when the tubing is mounted adjacent the occlusion sensor, and wherein the collar limits the distance that the movable plunger extends through the opening in the collar and protrudes into the tubing; f) a pump to which the occlusion sensor is connected and a cassette for receiving tubing of an infusion set, wherein the cassette connects to the pump; g) the cassette comprising at least one retaining member, and wherein the biasing mechanism biases the collar into engagement with the at least one retaining member; h) the occlusion sensor extending through the pump; i) structure to generate a warning signal and the warning signal includes at least one of the alarms selected from the group consisting of a visual alarm, audible alarm, and physical alarm; j) the occlusion sensor mounted to a pump and wherein the occlusion sensor is configured such that a sufficient change in the magnitude of the force applied to the sensor causes the pump to turn off; and/or k) sensor mounted on a circuit board; or any combination thereof.

According to aspects of the present invention an infusion system may have a pump configured to receive tubing of an infusion set, a sensor system disposed on the pump, the sensor system comprising a sensor and a plunger disposed to extend away from the sensor to transmit force from the tubing of the infusion set to the sensor wherein when tubing of an infusion set is mounted on the pump, the tubing exerts a force on the sensor via the plunger, the force changing relative to the pressure in the infusion set. The infusion system may also have: a) a sensor configured to generate a warning signal to indicate improper operation of the infusion system when the pressure inside the infusion system is above or below desired operational parameters; b) the sensor disposed on a circuit board and the plunger forced against the sensor responsive to pressure in the tubing; c) a collar having an opening, wherein the plunger extends through the opening; d) an infusion set comprising tubing and a cassette which holds the tubing to the pump; e) the cassette operably connected to the pump in a recessed location formed on the pump; f) a collar disposed adjacent the plunger and wherein the cassette has retaining members, and the collar engaging the retaining members when the cassette is operably connected to the pump; the sensor mounted to the pump using a mounting plate and a biasing mechanism; and/or g) wherein the force exerted on the sensor by the plunger is converted into a voltage output and wherein the voltage output varies based on the force applied by the plunger to the sensor; or any combination thereof.

A method of the invention may include detecting an occlusion in tubing by selecting an infusion pump having a sensor disposed thereon and a plunger disposed in communication with the sensor to transfer force to the sensor; connecting tubing of an infusion set adjacent the infusion pump so that the tubing is in communication with the plunger to thereby change the force transferred by the plunger to the sensor; and detecting an occlusion by measuring changes in pressure within the tubing communicated to the sensor via the plunger. The method may also include a) the step of selecting a cassette configured to receive the tubing of the infusion set and attaching the cassette to the infusion pump; b) the step of attaching the occlusion sensor to the infusion pump using a biasing mechanism; c) selecting a sensor formed by a piezoresistive sensor and having a collar with an opening for receiving the plunger; d) attaching the cassette to the infusion pump causes at least one retaining member of the cassette to come into engagement with the collar; e) the step of sending a warning signal when a sufficiently large change in the pressure inside the tubing is detected; and/or f) detecting an occlusion in the tubing by measuring the amount of force exerted on the sensor by the expansion or compression of the tubing, or any combination of the above.

A sensor system for use on a pump which pumps fluid through a tubing with the system having a pump having a pump body; and a sensor attached to the pump body and having a biasing mechanism which biases the sensor toward tubing when tubing is mounted on the pump. The sensor system may also include: a) a plungerplunger disposed adjacent the sensor for transferring force to the sensor; b) support structure adjacent the plungerplunger; c) a collar which may have an opening and wherein the plungerplunger extends through the opening; and/or d) sensor disposed on a printed circuit board, or any combination thereof or combinations discussed above.

There is thus disclosed an occlusion sensor and method of use. It will be appreciated that numerous changes may be made to the present invention without departing from the scope of the claims. The appended claims are intended to cover such modifications.

What is claimed is:

1. A pressure sensor system comprising:
   a sensor for measuring the pressure inside a structure;
   a movable plunger disposed in communication with the structure and the sensor, wherein the movable plunger applies a force against the sensor and is oriented so that, the magnitude of the force applied to the sensor by the movable plunger changes relative to a change in pressure inside the structure; and
   a biasing mechanism which biases the sensor toward the plunger;
   wherein the structure comprises tubing of an infusion set;
   wherein the sensor is disposed on a pump having a pump mechanism, and wherein the tubing is positioned adjacent the sensor and the pump such that the tubing is in communication with the movable plunger and the pump mechanism.

2. The system of claim 1, further comprising a pump body and wherein the sensor is attached to the pump body so as to allow movement of the sensor relative to the pump body.

3. The pressure sensor system according to claim 1, further comprising a collar, wherein the movable plunger extends through an opening in the collar to contact the structure whose pressure is being measured.

4. The pressure sensor system according to claim 3, wherein the structure is tubing of an infusion set and wherein the sensor further comprises a collar disposed about the plunger and a biasing mechanism which biases the sensor toward the plunger and biases the collar into engagement with tubing when the tubing is mounted adjacent the sensor, and wherein the collar limits the distance that the movable plunger extends through the opening in the collar and protrudes into the tubing.

5. The pressure sensor system according to claim 4, wherein the plunger partially collapses the tubing in an ambient state.

6. A system for measuring pressure including the sensor system according to claim 3, and further comprising a pump to which the sensor is connected and a cassette for receiving tubing of an infusion set, wherein the cassette connects to the pump.

7. The system for measuring pressure according to claim 6, further comprising a biasing mechanism which biases the sensor toward the plunger, wherein the cassette comprises at least one retaining member, and wherein the biasing mechanism biases the collar into engagement with the at least one retaining member.

8. The system for measuring pressure according to claim 7, wherein the retaining member limits movement of the tubing in a directional generally perpendicular to the movement of the plunger.

9. The pressure sensor system of claim 1, wherein the sensor is directly mounted on a circuit board.

10. An infusion system comprising:
a pump configured to receive tubing of an infusion set; and
a sensor system disposed on the pump, the sensor system comprising a sensor and a plunger disposed to extend away from the sensor to transmit force from the tubing of the infusion set to the sensor;
wherein when tubing of an infusion set is mounted on the pump, the tubing exerts a force on the sensor via the plunger, the force changing relative to the pressure in the infusion set;
wherein the sensor is mounted to the pump using a mounting plate and a biasing mechanism to allow the sensor to move relative to the pump.

11. The infusion system according to claim 10, wherein the sensor is directly disposed on a circuit board and the plunger is forced against the sensor responsive to pressure in the tubing.

12. The infusion system according to claim 10, further comprising a collar having an opening, wherein the plunger extends through the opening.

13. The infusion system according to claim 10, further comprising an infusion set, the infusion set comprising tubing and a cassette which holds the tubing to the pump.

14. The infusion system according to claim 13, further comprising a collar disposed adjacent the plunger and wherein the cassette has retaining members, and wherein the collar engages the retaining members when the cassette is operably connected to the pump.

15. The infusion system according to claim 14, wherein the retaining members contact the collar and limit expansion of the tubing.

16. The infusion system according to claim 10, further comprising an infusion set having tubing and wherein the plunger partially collapses the tubing in an ambient state.

17. An sensor system for used on a pump which pumps fluid through a tubing, the system comprising:
a pump having a pump body; and
a sensor attached to the pump body and having a biasing mechanism which biases the sensor toward tubing when tubing is mounted on the pump;
wherein the system comprises a plunger disposed adjacent the sensor for transferring force to the sensor.

18. The sensor system of claim 17, wherein the system comprises a support structure adjacent the plunger.

19. The sensor system of claim 18, wherein the support structure is a collar.

20. The sensor system of claim 19, wherein the collar has an opening and wherein the plunger extends through the opening.

21. The sensor system of claim 17, wherein the sensor is disposed on a printed circuit board.

* * * * *